(12) United States Patent
Hiro

(10) Patent No.: US 6,174,163 B1
(45) Date of Patent: Jan. 16, 2001

(54) METHOD OF FITTING BRACKET FOR ORTHODONTIC APPLIANCE

(76) Inventor: Toshiaki Hiro, 142-7 Ohaza Hirooka-Kataishi, Shiojiri-shi, Nagano-ken, 399-0705 (JP)

( * ) Notice: Under 35 U.S.C. 154(b), the term of this patent shall be extended for 0 days.

(21) Appl. No.: 09/308,771
(22) PCT Filed: Sep. 24, 1998
(86) PCT No.: PCT/JP98/04307
  § 371 Date: Jul. 23, 1999
  § 102(e) Date: Jul. 23, 1999
(87) PCT Pub. No.: WO99/16379
  PCT Pub. Date: Apr. 8, 1999

(30) Foreign Application Priority Data

Sep. 26, 1997 (JP) .................................................. 9-261228

(51) Int. Cl.⁷ .................................................. A61C 3/00
(52) U.S. Cl. .................................................. 433/24
(58) Field of Search ...................... 433/24, 196

(56) References Cited

U.S. PATENT DOCUMENTS

| | | |
|---|---|---|
| 3,738,005 | 6/1973 | Cohen et al. . |
| 4,014,096 * | 3/1977 | Dellinger .................... 433/24 |
| 4,284,405 * | 8/1981 | Dellinger .................... 433/24 |
| 4,526,540 * | 7/1985 | Dellinger .................... 433/24 |
| 4,551,096 * | 11/1985 | Dellinger .................... 433/24 |
| 4,657,508 * | 4/1987 | Dellinger .................... 433/24 |
| 5,055,039 * | 10/1991 | Abbatte et al. ............. 433/24 |
| 5,114,339 * | 5/1992 | Guis ............................ 433/24 |

FOREIGN PATENT DOCUMENTS 4-295352  10/1992  (JP) .

* cited by examiner

Primary Examiner—Todd E. Manahan
(74) Attorney, Agent, or Firm—Burns, Doane, Swecker & Mathis, L.L.P.

(57) ABSTRACT

An individual resin core used for a bracket fitting method of an orthodontic appliance includes an advance potion packed between a base of a bracket and a tooth and a core portion extending from the advance portion and covering a portion up to a cut edge of the tooth or occlusal surface. The core is individually formed for each tooth. Because this individual core has a low flexibility and is divided for each tooth, distortion and floating do not occur when it is fitted to the tooth of a patient, and the bracket can be bonded correctly. Since the resin core is independent of the alignment of teeth, it can be formed on a set up tooth impression. Since the bracket need not be returned to an original impression mold, technical work that would otherwise be necessary can be eliminated.

2 Claims, 6 Drawing Sheets

METHOD OF FITTING BRACKET FOR ORTHODONTIC APPLIANCE

TECHNICAL FIELD

The present invention relates to a bracket fitting method of an orthodontic appliance to be used for correcting teeth.

BACKGROUND OF THE ART

The orthodontic appliance is fitted by bonding its bracket to the tongue side face of a tooth of a patient. Since the tongue side face of the tooth has a more complicated shape than that of a lip side face, it is difficult to bond the bracket to an ideal position.

In order to bond the bracket to the ideal position on the tongue side face of the tooth, there has been adopted an indirect bonding method using the T.A.R.G. (Torque Angulation Reference Guide) or the C.L.A.S.S. (Custom Lingual Appliance Setup System). When the bracket is to be bonded to the tooth of the patient, according to that method, three to six teeth are individually bonded by using a bracket fitting core (or indirect tray) made of a flexible member such as silicone.

In the C.L.A.S.S., on the other hand, there is used a set-up tooth impression in which the tooth impression of the patient is re-arrayed into a target state, so that the bracket can be positioned more correctly than the T.A.R.G. This set-up tooth impression is prepared by forming a duplicate mold from the original impression mold of the tooth impression of the patient and by dividing the duplicate mold into individual teeth to re-array them.

In order to form the indirect tray by using the set-up tooth impression, the bracket is positioned at first with respect to the set-up tooth impression by using a gauge or the like, and the gap between the positioned bracket and the mold is filled with an adhesive (or an advance adhesive). As a result, the base face of the bracket is formed to conform to the tongue side face intrinsic to each tooth (advance of bracket). Next, the bracket positioned with respect to the set-up tooth impression is returned to the original impression mold, and the indirect tray is formed by covering the original impression mold with the silicone.

The indirect tray over all the teeth is usually divided into those for three to six teeth. Then, the adhesive is applied to the base face of the advanced bracket, and the indirect tray is fitted to the teeth of the patient, so that the bracket is bonded to the teeth of the patient. Finally, the indirect tray is removed from the bracket.

However, the indirect tray of the prior art has the following problems.

First of all, in both the T.A.R.G. and the C.L.A.S.S., the indirect tray extends over the three to six teeth and has flexibility so that it is liable to distort. This may cause a displacement of the bracket when this bracket is fitted to the teeth of the patient.

At the fitting time, on the other hand, the tray may distort to float the base of the bracket from the teeth of the patient. This makes it necessary to apply more adhesive to ensure the adhesion and fitting. If much adhesive is applied to the bracket, however, the excess adhesive will exude from the fitting face. This makes a work necessary for removing the excess adhesive.

Since the indirect tray of the prior art has a size to extend over the three to six teeth, moreover, it has to be supported till the adhesive sets after it was fitted to the teeth of the patient, so that it may go out of position.

Since the indirect tray of the prior art samples not only the tooth shape of the patient but also the alignment of teeth, still moreover, it cannot be used if the tooth alignment of the patient changes after the sampling of the tooth impression of the patient and before the fitting of the bracket. For this time period, therefore, it is impossible to extract or separate the tooth.

Next, according to the method using the C.L.A.S.S., the bracket has to be returned to the original impression mold after it was advanced with the set-up tooth impression. Since the original impression mold has to be left as it is, therefore, a duplicate is required for forming the set-up to the impression.

In order to return the bracket to the original impression mold, on the other hand, complicated technical works are required for making a person tray or for forming a notch or mark in the original impression mold. With these troubles, the bracket may goes out of position when it is returned to the original impression mold.

DISCLOSURE OF THE INVENTION

In order to solve the aforementioned problems, an object of the invention is to provide a bracket fitting method and a bracket fitting core of an orthodontic appliance which is enabled to position correctly by fitting a bracket for each tooth.

According to the invention, there is provided an orthodontic bracket fitting method of an orthodontic appliance for correcting each tooth of a patient by fitting the base of an orthodontic bracket individually to the tooth and by extending an orthodontic wire between the orthodontic brackets. First of all, the orthodontic brackets are individually positioned to the individual tooth of the impression mold of the patient. Next, each tooth of the impression mold is with a resin in an unset state, to form individually for each tooth a bracket fitting individual resin core which is integrally molded of an advance portion packed between the tooth and the base of said bracket positioned with respect to said tooth, and a core portion extending from said advance portion to a cut edge of the tooth or an occlusal surface. Then, said bracket fitting individual resin core in the state integrated with said bracket is taken out from each tooth of said impression mold and is fitted and bonded to each corresponding tooth of the patient. Finally, each bracket fitting individual resin core is removed.

In the invention, the individual resin core is used as the bracket fitting core. This individual resin core is formed of a resin having little flexibility for each tooth so that no distortion occurs when it is fitted to the tooth of the patient. As a result, the bracket can be correctly positioned on the tooth of the patient.

Since no distortion occurs, on the other hand, the advance portion for the fitting face does not flat from the tooth of the patient. As a result, the bonding can be ensured with a small amount of adhesive so that the exudation of the adhesive is eliminated to make it unnecessary to remove the excess adhesive.

Since this individual resin core is formed individually for each tooth, it is simply shaped to cover the bracket fitting face of the tooth and the cut edge of the tooth or an occlusal surface so that it can be taken out without any breakage from the mold even if it has little flexibility.

On the other hand, the individual resin core is small and light because it is formed individually for each tooth. This makes it unnecessary to support the individual resin core till the adhesive is set after it was fitted to the tooth of the patient.

Since the individual resin core samples the shape of each tooth of the patient and has no relation to the alignment of teeth of the patient, moreover, it can be fitted even if the alignment of teeth of the patient changes for the time period from the sampling of the tooth impression of the patient to the fitting of the bracket. For this time period, therefore, a treatment such as a tooth extraction or separation can be made.

When this individual resin core is formed using the C.L.A.S.S., on the other hand, the alignment of teeth has no relation so that the bracket need not be returned to the original impression mold after the bracket was advanced with the set-up tooth impression. This makes it possible to eliminate the technical work which might otherwise be required for making a personal tray or for forming a notch or mark in the original impression mold. On other hand, there arises no problem of the positional displacement which might otherwise occurs when the bracket is returned to the original impression mold.

Thus, the duplicate mold can be eliminated, said impression mold can be exemplified by a set-up tooth impression which is prepared by dividing the original impression mold of the patient for each tooth and by re-arraying it to a target alignment of teeth.

On the other hand, said orthodontic bracket can be positioned with respect to the impression mold of the patient by bending an orthodontic wire in conformity with said set-up tooth impression and then by fitting said wire to each of said brackets.

Thus, the positioning of the bracket can be performed more simply than that using a meter such as a gauge, and the wire thus used can be actually used for a treatment as a finishing wire.

BEST MODE FOR CARRYING OUT THE INVENTION

A bracket fitting method and a bracket fitting core of an orthodontic appliance according to the invention will be described with reference to the accompanying drawings.

Figure 1:
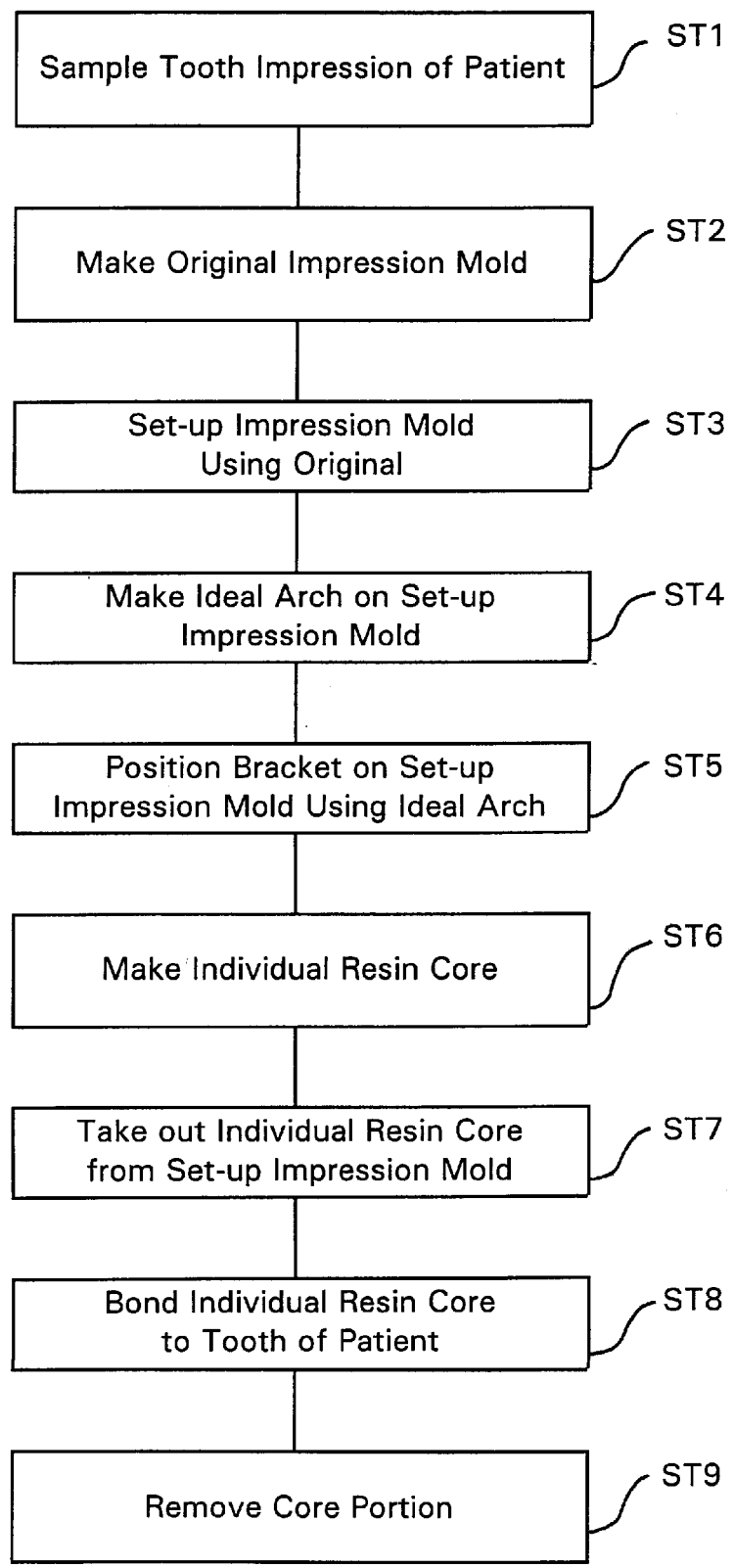
FIG. 1 is a flow chart showing a bracket fitting method of an orthodontic appliance of the invention.

FIG. 1 is a flow chart showing one embodiment of the bracket fitting method of the orthodontic appliance of the invention.

Figure 2:
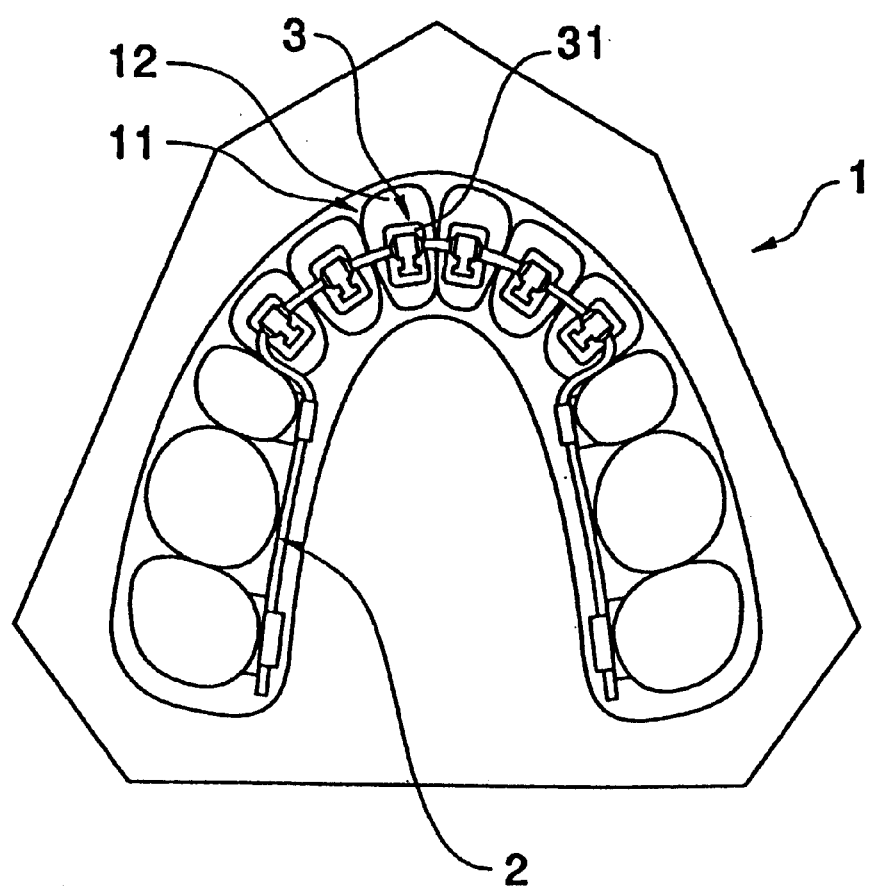
FIG. 2 is an explanatory diagram showing the state in which a bracket is positioned in a set-up tooth impression.

At first Step ST1, the tooth impression of a patient is sampled. Here are used an AG impression agent and a manufactured impression tray for a toothed jaw. At Step ST2, an original impression mold is made of hard gypsum using that tooth impression. At Step ST3, the original impression mold is parted to make a set-up tooth impression 1 which is re-arrayed to a target alignment of teeth, as shown in FIG. 2.

With this set-up tooth impression 1, there is positioned an orthodontic bracket 3 in the orthodontic appliance. For this positioning, an orthodontic rectangular wire 2 of full size is bent to the tongue side face 12 of a tooth 11 of the set-up tooth impression 1 to make an ideal arch (at Step ST4). To the bent rectangular wire 2, moreover, there are individually bonded the brackets 3 corresponding to the individual teeth, to position the individual brackets 3 correctly with respect to the individual teeth 11 (at Step ST5).

Figure 3:
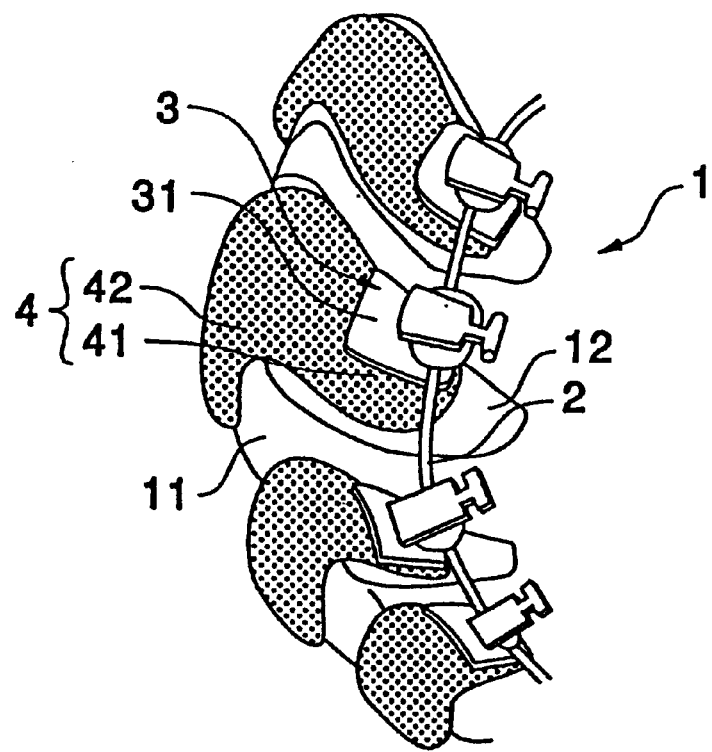
FIG. 3(a) is an explanatory diagram showing the state in which an individual resin core of the invention is formed on the set-up tooth impression.
FIG. 3(b) is an explanatory diagram showing the state in which the individual resin core shown in (a) is seen from the side face.
Figure 3:
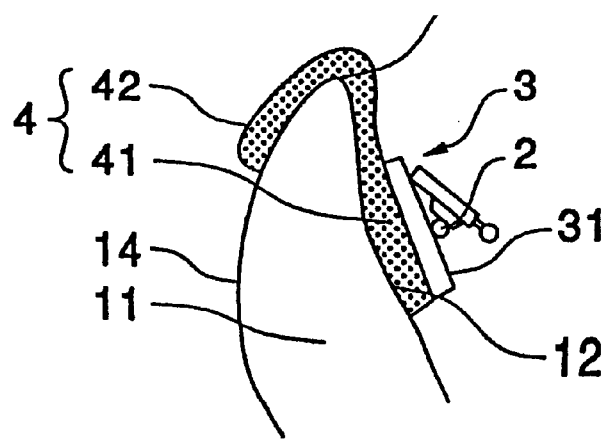
Figure 4:
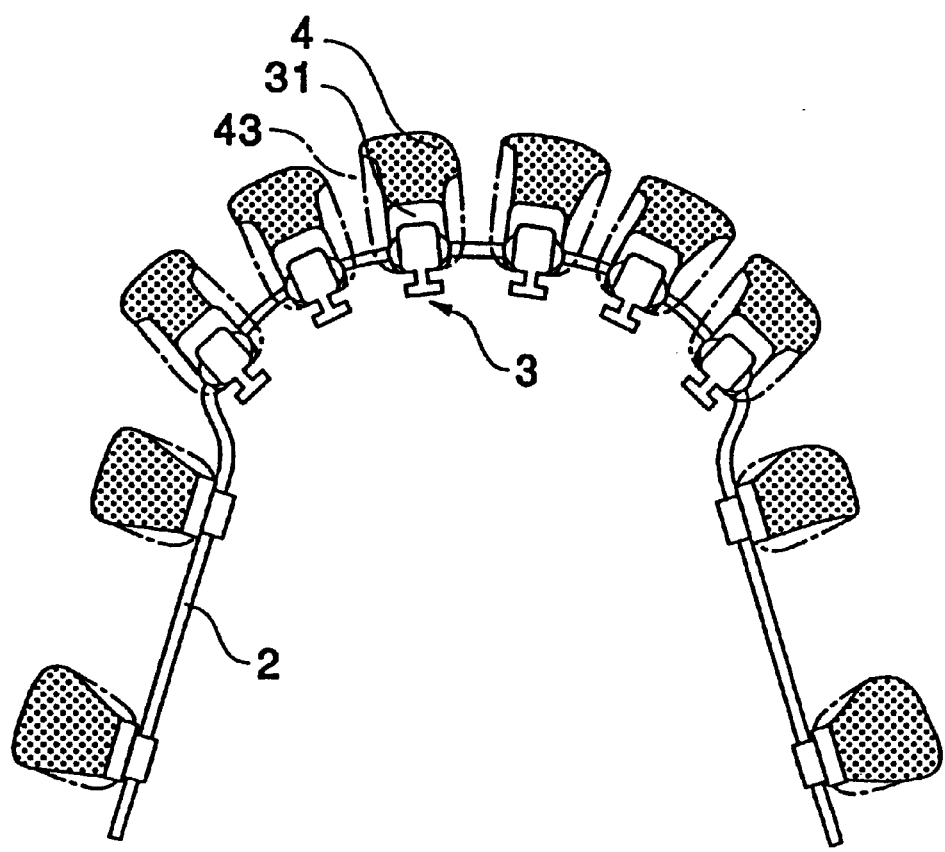
FIG. 4 is an explanatory diagram showing the state in which the individual resin core is parted from the set-up tooth impression.

Next, as shown in FIG. 3(a), an individual resin core 4 for fitting the bracket is made (at Step ST6). For this, one layer of gypsum separating liquid of calcium alginate is applied to each tooth 11 of the set-up tooth impression 1. Moreover, a cold-polymerizable resin in an unset state is laminated individually on each tooth 11 of the set-up tooth impression 1 by means of a brush to form an advance portion 41 packed between the base 31 of the bracket 3 and the tongue side face of the tooth 11, as shown in FIG. 3(b).

This advance portion 41 is fixed on the base 31 of the bracket 3. The resin is further extended upward to form a core portion 42. This core portion 42 is extended upward from the advance portion 41 along the tongue side face 12 of each tooth 11 and is folded back to cover a cut edge 13 (or an occlusal surface in the case of a molar tooth) of the tooth up to the upper side of a lip side face 14 of the tooth 11 in a small thickness.

The advance portion 41 and the core portion 42 are formed to have inner faces in close contact with the tooth 11 so that they provide a negative mold for the tooth 11. This negative mold is so wide as to slightly extend sideways of the base 31 of the bracket 3, as shown in FIG. 3(a), but is narrower than each tooth 11. Thus, the individual resin core 4 has the advance portion 41 and the core portion 42 integrally molded and is formed individually for each tooth.

After the individual resin core 4 was set, it is individually taken off or removed integrally with the bracket 3 from each tooth 11 of the set-up tooth impression 1 (at Step ST7). Although the individual resin core 4 fitted to the bracket 3 has neither flexibility nor a play with respect to each tooth 11, it is divided for each tooth and has such a simple shape as to cover the bracket fitting face of the tooth and the cut edge of the occlusal surface so that it can be taken out without breakage from the set-up tooth impression 1. Here, an unnecessary resin 43, as exuded sideways of the base 31 of the bracket 3, is removed.

Figure 5:
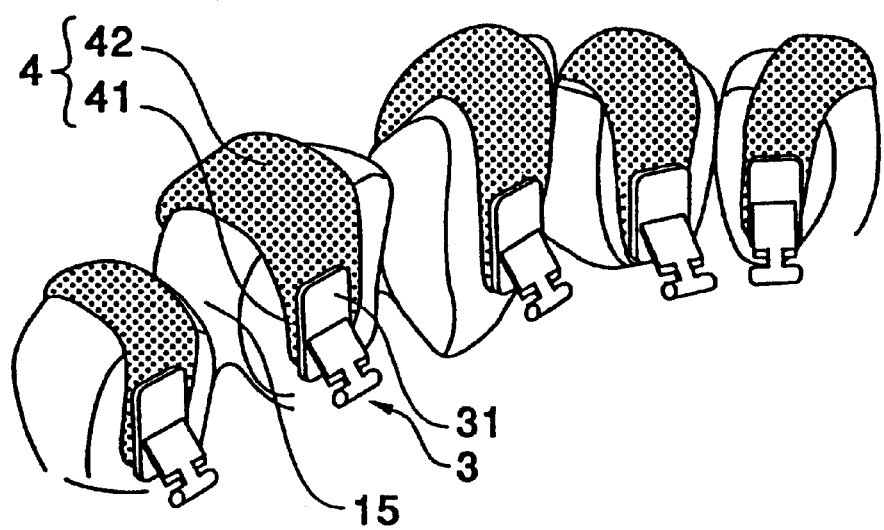
FIG. 5 is an explanatory diagram showing the state in which the individual resin core is bonded to the tooth of a patient.

As shown in FIG. 5, each individual resin core 4 is bonded to each tooth 15 of the patient (at Step ST8). Although each tooth 15 of the patient is oriented in a direction different from that of each tooth 11 of the set-up tooth impression 1, the individual resin core 4 is formed individually for each tooth and has no relation to the alignment of teeth so that it can be fitted. Thus, the bracket 3 can be fitted to each tooth 15 of the patient while being guided by the individual resin core 4. The adhesive is applied exclusively to the advance portion 41 of the individual resin core 4.

Here, the individual resin core 4 has little clearance from the tooth 15 and a proper hardness so that no distortion occurs when it is fitted to the tooth 15. As a result, the individual resin core 4 can be correctly fitted to the bracket 3. Since the individual resin core 4 is not caused to float from the tooth 15 of the patient by the distortion, on the other hand, it can be reliably bonded even with a small amount of adhesive while preventing the adhesive from exuding. Since the individual resin core 4 is made small and light for each tooth, on the other hand, it will not go out of position even if it is released before the adhesive is completely set.

Figure 6:
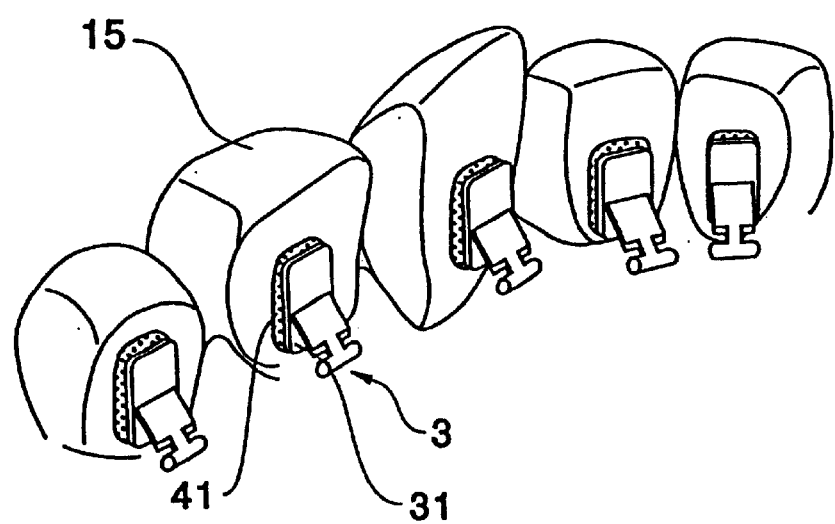
FIG. 6 is an explanatory diagram showing the state in which the fitting of the bracket was completed.

After the adhesive was set, a round bar of steel is used to form a cut between the advance portion 41 and the core portion 42 to remove the core portion 42 from the individual resin core 4 (at Step ST9). As a result, the bracket 3 is bonded to the tooth 15 of the patient through the advance portion 41, as shown in FIG. 6, so that little portion exudes from the base 31 of the bracket 3. Thus, the fitting of the bracket 3 is ended.

Here in this embodiment, the cold-polymerizable resin is used for the individual resin core but may be replaced by another. On the other hand, the fitting position of the bracket should not be restricted on the tongue side face but may be located on the lip side face. Moreover, this embodiment is applied to the C.L.A.S.S. but can also be applied to the T.A.R.G.

INDUSTRIAL APPLICABILITY

According to the method of the invention, as has been described hereinbefore, the bracket fitting individual resin core is used. This core is made of a resin having little flexibility and is formed individually for each tooth.

Since no distortion occurs when the individual resin core is fitted to the tooth of a patient, therefore, the bracket can be correctly positioned on the tooth of the patient. Since the individual resin core is not distorted so that the advance portion or the bonding surface does not float from the tooth of the patient, on the other hand, the individual resin core can be bonded with a small amount of adhesive so that little adhesive exudes to make it unnecessary to remove the excess adhesive.

Moreover, the individual resin core is a sample of the shape of each tooth of the patient and is independent of the alignment of teeth of the patient so that it can be fitted even if the tooth of the patient moves during the time period from the sampling of the tooth impression of the patient to the bonding of the bracket. Even for this time period, therefore, a treatment such as a tooth extraction or separation can be made. Like this, when the patient has a serious crowding or torsion in the teeth, the individual resin core can be bonded after the teeth are once leveled to some extent by a temporary bracket so that the bracket can be fitted in position.

On the other hand, since this individual resin core has no relation to the alignment of teeth, even in case where the resin core is formed using C.L.A.S.S., the bracket need not be returned to the original impression mold after it was advanced by the set-up tooth impression. This makes it possible to eliminate the technical work such as a making of a personal tray or a forming of a notch in the original impression mold. On the other hand, the problem of a positional displacement, as might otherwise be caused when the bracket is returned to the original impression mold, is solved.

Moreover, no duplicate mold is necessary so that the set-up tooth impression can be formed by dividing the original impression mold itself.

The positioning of the bracket with respect to the set-up tooth impression can be performed more simply than that using a measure such as a gauge, if the bracket is positioned by bending the orthodontic wire and by fitting it to the wire. On the other hand, the wire thus used can be fitted as a finishing arch to the bracket bonded to the tooth of the patient.

What is claimed is:

1. An orthodontic bracket fitting method of an orthodontic appliance for correcting each tooth of a patient by fitting the base of an orthodontic bracket individually to the tooth and by extending an orthodontic wire between the orthodontic brackets, said method comprising:

positioning the orthodontic brackets individually to the individual tooth of the impression mold of the patient;

individually feeding each tooth of the impression mold with a resin in an unset state, to form individually for each tooth a bracket fitting individual resin core which is integrally molded to include an advance portion packed between the tooth and the base of said bracket positioned with respect to said tooth, and a core portion extending from said advance portion to a cut edge of the tooth or an occlusal surface;

removing said bracket fitting individual resin core in the state integrated with said bracket from each tooth of said impression mold;

fitting and bonding each of said removed bracket fitting individual resin cores to each corresponding tooth of the patient; and thereafter, removing at least a portion of each bracket fitting individual resin core from the tooth.

2. An orthodontic bracket fitting method of an orthodontic appliance as set forth in claim 1, wherein:

said impression mold is a set-up tooth, the impression of which is prepared by dividing the original impression mold of the patient for each tooth and by re-arraying it to a target alignment of teeth; and said orthodontic bracket is positioned with respect to the impression mold of the patient by banding an orthodontic wire in conformity with said set-up tooth impression and then by fitting said wire to each of said brackets.

* * * * *